United States Patent [19]

Crainich

[11] Patent Number: 5,407,293
[45] Date of Patent: Apr. 18, 1995

[54] COUPLING APPARATUS FOR MEDICAL INSTRUMENT

[76] Inventor: Lawrence Crainich, P.O. Box 996, Charlestown, N.H. 03603

[21] Appl. No.: 55,639

[22] Filed: Apr. 29, 1993

[51] Int. Cl.⁶ .............................................. B25G 3/00
[52] U.S. Cl. .................................... 403/322; 403/325; 403/327; 403/348; 403/350; 403/353; 604/22
[58] Field of Search .............. 403/322, 325, 327, 348, 403/349, 350, 353, 354; 604/22, 167, 180

[56] References Cited

U.S. PATENT DOCUMENTS

| | | | |
|---|---|---|---|
| 271,143 | 1/1883 | Smith | 403/350 |
| 930,169 | 8/1909 | Exley | 403/350 |
| 1,033,187 | 7/1912 | Metzger | 403/349 |
| 1,099,670 | 6/1914 | Shoffner | 403/349 |
| 1,171,380 | 2/1916 | Arthur | 403/349 |
| 4,632,437 | 12/1986 | Robson et al. | 403/350 |
| 4,705,038 | 11/1987 | Sjostrom et al. | 604/22 |
| 4,986,690 | 1/1991 | Cooksey | 403/348 |
| 5,052,849 | 10/1991 | Zwart | 403/349 |

FOREIGN PATENT DOCUMENTS

| | | | |
|---|---|---|---|
| 1141155 | 8/1957 | France | 403/349 |
| 2662755 | 12/1991 | France | 403/349 |
| 2663691 | 12/1991 | France | 403/349 |
| 585325 | 12/1977 | U.S.S.R. | 403/349 |

Primary Examiner—Richard A. Bertsch
Assistant Examiner—Howard R. Richman
Attorney, Agent, or Firm—Bachman & LaPointe

[57] ABSTRACT

A coupling apparatus for a medical instrument includes an insertion member having a protruding portion; a receiving member sized to receive the protruding portion of the insertion member; an engaging structure having a ridge member and a groove member for coupling the insertion member with the receiving member, one of the ridge member and the groove member being disposed on the insertion member, and the other being disposed on the receiving member, the ridge member having a ridge portion and the groove member having a groove portion, rotatable relative to one another between an engaged position wherein the ridge portion and the groove portion are engaged against longitudinal separation, and a disengaged position wherein the groove portion can be longitudinally separated from the ridge portion; and a locking member for retaining the ridge portion and the groove portion in the engaged position.

17 Claims, 3 Drawing Sheets

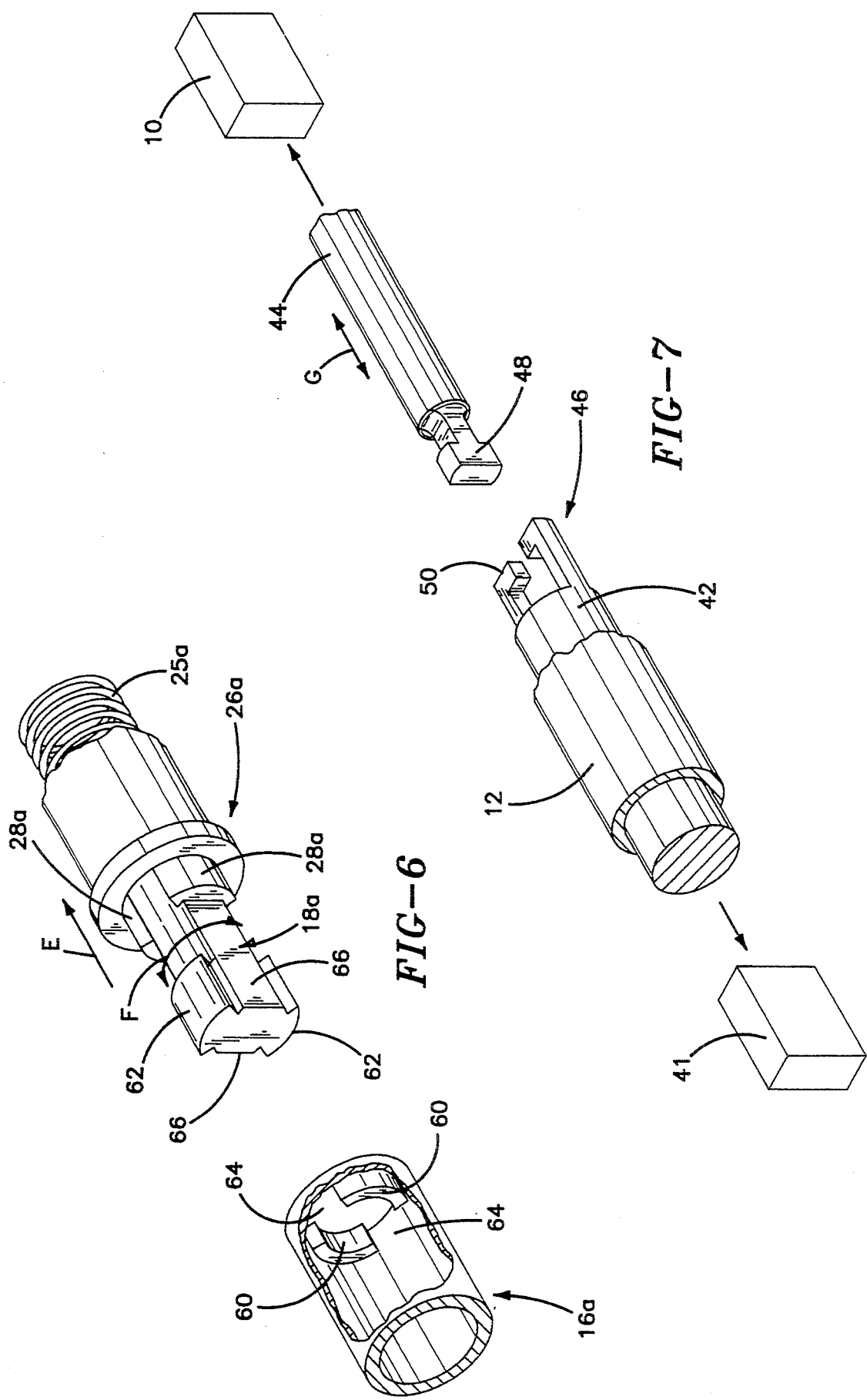

COUPLING APPARATUS FOR MEDICAL INSTRUMENT

BACKGROUND OF THE INVENTION

The invention relates to the field of instruments, especially medical instruments and, more particularly, to a coupling apparatus for coupling a tool portion of a medical instrument to a handle portion thereof. The apparatus is particularly suitable for coupling laparascopic instruments.

Conventional couplings for medical instruments involve threaded assemblies and the like which render the connection of tool head to handle practically permanent or cumbersome for quick assembly and disassembly. This is, of course, desirable so as to avoid the separation of the tool and handle during use in a surgical procedure.

In the interests of sterility, sharpness and the like, however, it is desirable for the tool portions of medical instruments to be readily exchangeable and, therefore, for the coupling and uncoupling of the tool head to the handle to be readily accomplished, and at the same time retained with rigidity. In this way, disposable tool heads can be utilized which can be conveniently removed and replaced after use.

Such a coupling would also be desirable so as to allow numerous tool heads to be used interchangeably as desired with a single handle piece.

Such a coupling would be still further desirable so that complex tool heads, which are not readily disposable, can be quickly and easily removed from the handle portion for sterilization, maintenance etc.

It is therefore the principal object of the present invention to provide a coupling apparatus for a medical instrument which allows convenient coupling and uncoupling of a tool head to a handle thereof.

It is a further object of the present invention to provide such a coupling which, when coupled, is secure so as to avoid inadvertent uncoupling of the instrument during use and to also achieve radial orientation.

Other objects and advantages will appear hereinbelow.

SUMMARY OF THE INVENTION

The foregoing objects and advantages are readily obtained by the presently disclosed invention, which comprises an insertion member having a rearwardly protruding portion; a receiving member sized to receive the protruding portion of the insertion member; engaging means, preferably including ridge means and groove means for coupling the insertion member with the receiving member, one of the ridge means and groove means being disposed on the insertion member and the other being disposed on the receiving member, the ridge means having a ridge portion and the groove means having a groove portion which are rotatable relative to one another between an engaged position wherein the ridge portion and the groove portion are engaged against longitudinal separation, and are radially oriented, and a disengaged position wherein the groove portion can be longitudinally separated from the ridge portion; and locking means for retaining the ridge and groove means in the engaged position.

The ridge portion may preferably comprise at least one ridge disposed around a portion of an outer circumference of the protruding portion of the insertion member.

The groove portion may preferably comprise a groove formed around a portion of an inside perimeter of the receiving member.

As will be seen, the present invention allows firm and releasable connection or coupling of a tool head to a handle member of a medical instrument so as to allow separation of the tool head for disposal, sterilization, sharpening, maintenance and/or replacement with the same or a different type of tool head.

BRIEF DESCRIPTION OF THE DRAWINGS

A detailed description of the preferred embodiments of the invention follows, with reference to the attached drawings, wherein:

FIG. 5 is an enlarged view of a portion of FIG. 4;

FIG. 6 is a perspective view, partially broken away, of an alternate embodiment of the invention;

FIG. 7 is a perspective view of an alternate embodiment of the invention including a drive rod coupling; and FIG. 8 is a perspective view of an alternate embodiment of the invention.

DETAILED DESCRIPTION

The invention relates to a coupling apparatus for medical instruments which allows convenient separation and reattachment of various components of a medical instrument. The coupling apparatus is especially useful in allowing the convenient separation and attachment of a tool head or operative element of the instrument and a handle member of the instrument.

Such separation and attachment is useful for numerous reasons including, but not limited to, replacing disposable or single use tool heads, removing tool heads for sterilization, sharpening, maintenance and exchanging one tool head for a like or different tool head as necessary.

Figure 1:
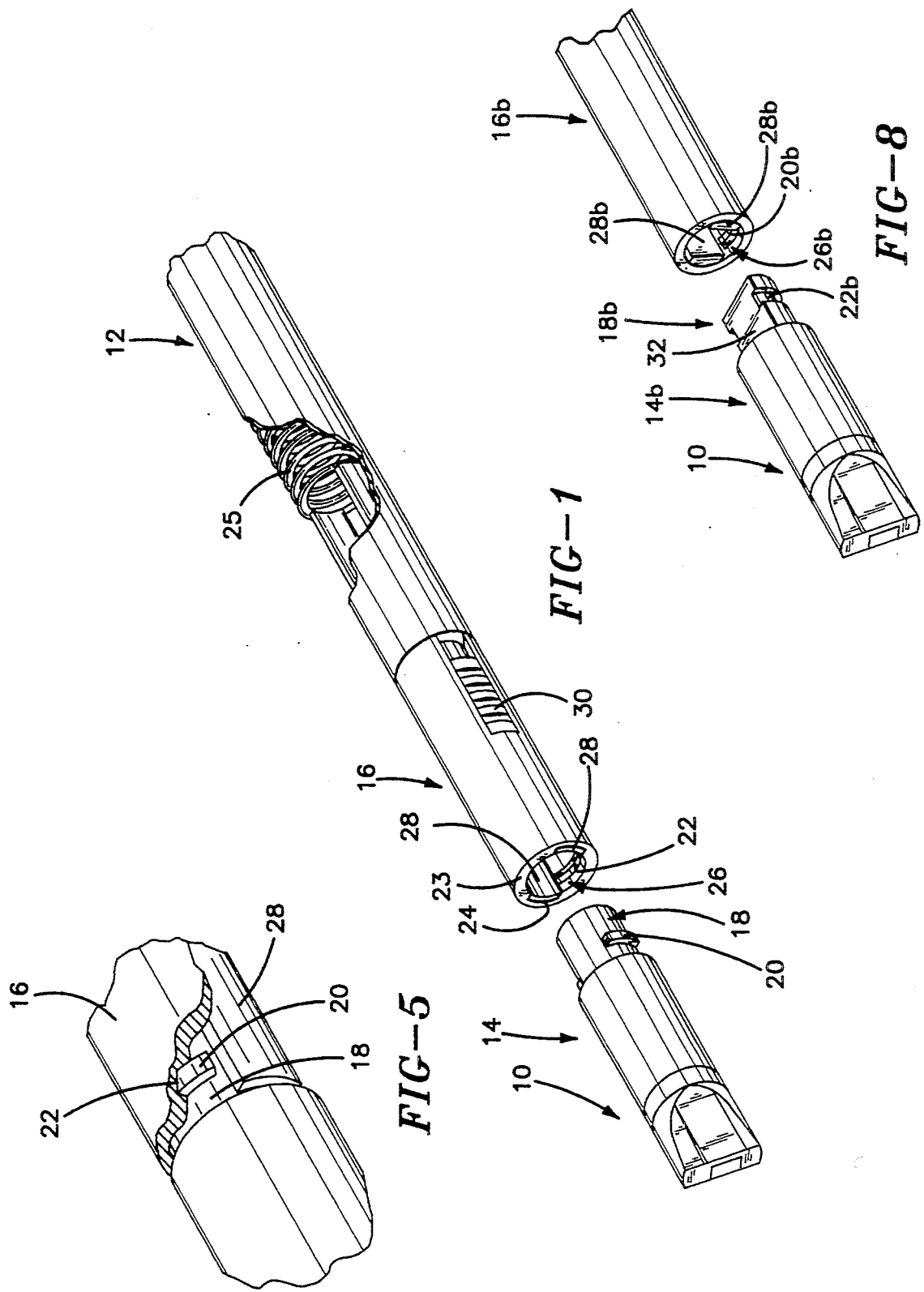
FIG. 1 is a perspective view of a medical instrument with coupling apparatus according to the invention.

Referring to FIG. 1, a preferred embodiment of the invention is shown. Tool head 10 is connected to handle 12, according to the invention, through a coupling apparatus which includes an insertion member 14 and a receiving member 16. The tool head 10 shown in FIG. 1 is a disposable cartridge for surgical staples. As set forth above, however, the coupling apparatus of the present invention is useful for the attachment of any desired tool head to a handle member.

Insertion member 14 preferably has a rearwardly protruding portion 18 which is sized to be received within receiving member 16.

Conventionally, the tool head would be connected to the handle through a thread connection or the like in such a manner as to render the connection practically permanent or at best cumbersome to remove and reattach.

According to the invention, however, insertion member 14 and receiving member 16 are releasably coupled through an engaging or ridge and groove structure which firmly and releasably couples the two elements.

As shown, protruding portion 18 preferably has a substantially cylindrical outer surface and has at least one projection or ridge 20 disposed around a portion of the outer surface.

Receiving member 16 preferably has a substantially cylindrical inner surface, as shown, and is preferably sized so as to snugly receive protruding portion 18. This fit is preferably provided with as narrow a tolerance as practical so as to avoid any wobble between tool head 10 and handle 12.

Receiving member 16 preferably has at least one groove 22 defined around a portion of the inner surface thereof. Receiving member 16 also preferably has at least one longitudinal cutout or track 24 defined longitudinally along the inner surface thereof to receive ridge 20 of protruding portion 18. Receiving member 16 has an edge 23 facing insertion member 14, and longitudinal track 24 extends to edge 23 so that track 24 can receive ridge 20. Longitudinal track 24 is preferably sized so as to accommodate ridge 20 of protruding portion 18. Thus, longitudinal track 24 preferably extends at least as far radially and circumferentially around the inner surface of receiving member 16 as does ridge 20 of protruding portion 18. Preferably, longitudinal tracks 24 are provided in a like number to the number of ridges 20 on protruding portion 18, and are also provided in similar circumferential spacing as ridges 20.

In this manner, ridges 20 can be aligned with tracks 24 at edge 23 so as to allow protruding portion 18 to be readily and freely inserted into receiving member 16.

Longitudinal tracks 24 intersect groove 22. In this manner, insertion member 14 can be inserted into receiving member 16, with ridges 20 lined up with tracks 24. Insertion member 14 can then be rotated relative to receiving member 16 so as to rotate ridges 20 into groove 22, thereby engaging insertion member 14 with receiving member 16, and radially orienting tool head 10. The steps of connecting and disconnecting insertion member 14 and receiving member 16 will be more thoroughly described below.

Figure 2:
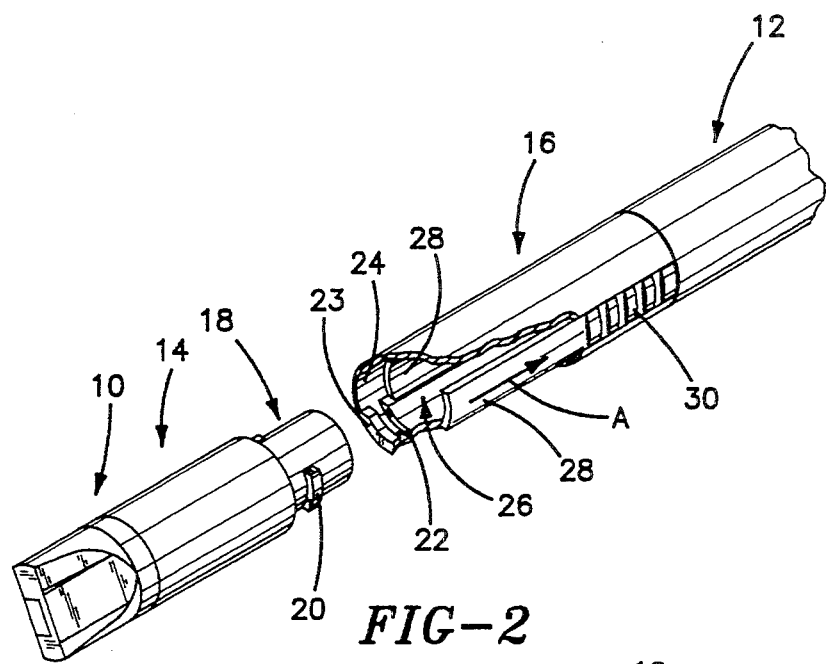
FIGS. 2–4 are partially cut away perspective views sequentially showing the connection of a coupling apparatus according to the invention.

Further according to the invention, at least one locking member 26 (also shown in FIG. 2) is preferably disposed in at least one track 24. Locking member 26 is preferably slidably disposed in receiving member 16 and is slidable between an extended position, as shown in FIG. 1, and a withdrawn position as shown in FIG. 2.

Returning to FIG. 1, locking member 26 may preferably have an arm 28 disposed in each track 24, and may be biased by any known and convenient means, such as spring 25, toward the extended position.

As shown in FIG. 1, when locking member 26 is in the extended position, arms 28 occupy tracks 24 at the point of intersection of track 24 and groove 22. That is, arms 28 extend into a plane of rotation of insertion member 14 relative to receiving member 16. Thus, when locking member 6 is in the extended position, with insertion member 14 inserted into receiving member 16, with ridges 20 rotated into groove 22, ridges 20 are retained in groove 22 and cannot be rotated out of groove 22 into track 24. Thus, when locking member 26 is in the extended position, the apparatus according to the invention is locked against rotation out of the engaged position, and is radially oriented.

Locking member 26 also preferably has a gripping portion 30 which is accessible from outside of the receiving member 16 so as to allow locking member 26 to be manipulated longitudinally between the extended position and the withdrawn position.

As will be more fully described below, locking member 26 is preferably slidable, toward a withdrawn position, to a point where locking member 26 no longer obstructs the point of intersection between tracks 24 and groove 22, as clearly shown in FIG. 2. In this manner, when locking member 26 is in the withdrawn position, protruding portion 18 with ridges 20 thereon can be readily inserted into or removed from receiving member 16 by rotation and withdrawal.

Arms 28 and ridges 20 may preferably be sized so that arms 28 abut both sides of ridge 20 when the apparatus is locked together so as to prevent rotation of tool head 10 relative to handle 12 and to maintain correct radial orientation thereof.

Referring to FIGS. 2-5, the steps of connecting the apparatus will be described.

A tool head 10 may be connected to handle 12 by first manipulating locking member 26 against spring 25, or simply compressing spring 25 to move arms 28 to the withdrawn position as indicated by arrow A of FIG. 2, wherein a portion of receiving member 16 is broken away to better illustrate the operation of the invention.

Figure 3:
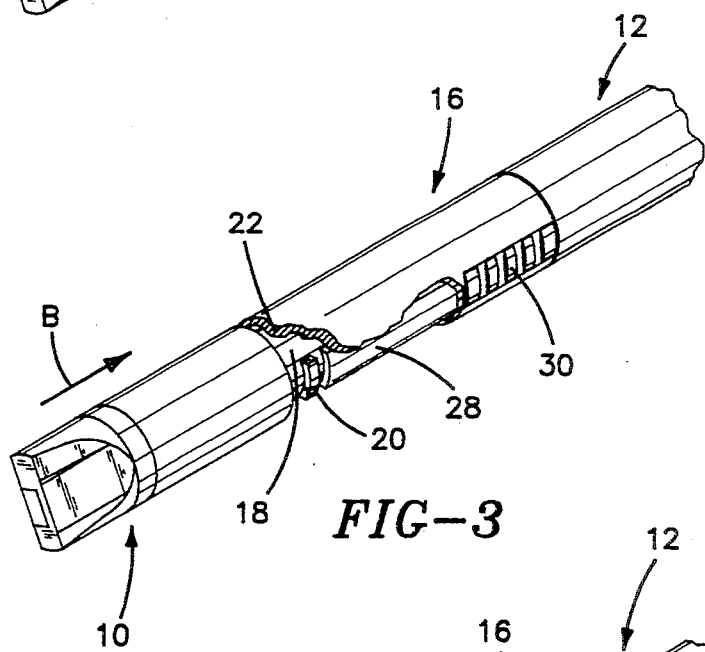

As shown in FIG. 3, ridges 20 are then aligned with tracks 24 at edge 23, and protruding portion 18 is inserted into receiving member 16 in the direction of arrow B in FIG. 3 with ridges 20 inserted into tracks 24.

Once protruding portion 18 is sufficiently inserted, ridges 20 align with groove 22 at the point of intersection of groove 22 and tracks 24. At this point, tool head 10 and insertion member 14 are rotated in either direction relative to receiving member 16, as shown by arrow C in FIG. 4. Ridges 20 enter and engage groove 22 from tracks 24 at the intersection of tracks 24 and groove 22, and exit that portion of track 24 through which arms 28 of locking member 26 extend when in the extended position. Locking member 26 is then manipulated, or released and biased by spring 25, to move arms 28 toward the extended position as shown by arrow D in FIG. 4. At this point, insertion member 14 is firmly locked into engagement with receiving member 16 and is securely held so as to avoid rotation to the disengaged position and/or inadvertent separation during use. FIG. 5 shows an enlarged portion of FIG. 4 to further illustrate the interlocking of ridge 20 and groove 22 in greater detail.

Figure 4:
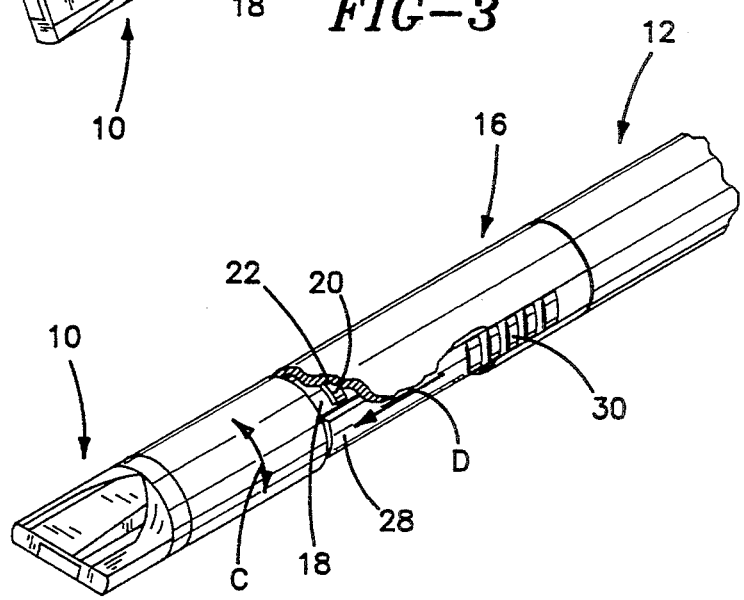

Separation of the apparatus is readily accomplished when desired by reversing the steps of FIGS. 2-4. That is, insertion member 14 and receiving member 16 may readily and easily be separated by withdrawing locking member 26 to move arms 28 away from the intersection of groove 22 and tracks 24, rotating insertion member 14 so as to align ridge 20 with track 24 and thereby disengage groove 22 and ridge 20, and longitudinally separating the two elements.

As can be appreciated, this structure allows easy separation of a tool head 10 from a handle 12 which separation is useful for a number of reasons as set forth above. Further, when tool head 10 is locked into handle 12, as shown in FIG. 4, the coupling is firm and secure so as to prohibit undesired separation or rotation of the tool head during use.

FIG. 6 illustrates a preferred embodiment wherein locking member 26a is slidably disposed on insertion member 14a.

Similarly to the first embodiment, locking member 26a has arms 28a which extend rearwardly, and is preferably biased rearwardly by biasing means such as spring 25a. FIG. 6 also illustrates an alternate embodiment of the engaging structure. As shown, the engaging structure may suitably comprise projecting sections 60, 62, disposed on receiving member 16a and insertion member 14a respectively. As shown, receiving member 16a may have two inwardly projecting sections 60 while insertion member 14a has two outwardly projecting sections 62. Sections 60 are preferably arranged so as to define spaces 64 therebetween, and correspondingly, sections 62 are preferably arranged so as to define spaces 66 therebetween. According to this embodiment, insertion member 14a can be inserted into receiving member 16a by aligning projecting sections 62 with spaces 64. Once fully inserted, rotation of insertion member 14a relative to receiving member 16a engages projecting sections 60, 62 behind each other so as to engage insertion member 14a and receiving member 16a against longitudinal separation. Sufficient rotation of insertion member 14a allows arms 28a of locking member 26a to extend into spaces 64 and thereby lock the device in the engaged position.

When the device of this embodiment is to be coupled, projecting sections 60 contact arms 28a of sliding member 26a and bias member 26a against spring 25a in the direction of arrow E. Once insertion member 14a is fully inserted, rotation of insertion member 14a in either direction as indicated by arrow F will engage projecting section 62 behind projecting section 60. Upon sufficient rotation, arms 28a of sliding member 26a will align with spaces 64, at which point spring 25a forces arms 28a into spaces 64 to lock the device. Locking member 26a is preferably slidably disposed on insertion member 14a in a non-rotatable manner so as to effectively lock insertion member 14a, and tool head 10 attached thereto but not shown in FIG. 6, in a rotationally fixed position. Such non-rotatable mounting may be accomplished through any suitable and convenient means. For example, such non-rotatable mounting may be provided by forming flats 52 along surfaces of insertion member 14a, and providing corresponding flats 54 on inner surfaces of locking member 26a. Flats 52, 54 cooperate or interact so as to prevent rotation of locking member 26a relative to insertion member 14a. Flats 52 are preferably formed along at least a portion of protruding portion 18.

An advantage of the embodiment of FIG. 6 is that the insertion member 14a and receiving member 16a can be both coupled and uncoupled using one hand, because locking member 26a is disposed on insertion member 14a. This allows manipulation of locking member 26a and rotation of insertion member 14a into and out of the engaged position to be performed with one hand.

Of course, the teachings of the present invention could be utilized to connect any type of tool head 10 to a handle 12 as desired. Thus, tool head 10 may include, for example, and not by way of limitation, a disposable cartridge for surgical staples, a trocar head, surgical scissors, or any laparascopic device or the like.

To the extent that the tool may require a mechanical drive of some sort, or may have an interior flow passage, insertion member 14 or 14a and receiving member 16 or 16a may preferably be hollow or tubular so as to accommodate either or both considerations. In this way, the coupling apparatus provides a continuous inner passage to allow fluid flow or the disposition of other medical instruments and/or drive mechanisms for the tool head.

Such a drive mechanism may include, for example, a simple drive or push/pull rod structure disposed through the continuous inner passage. FIG. 7 illustrates a connection, according to the invention, for use with such a drive rod 46. Drive rod 46 would suitably be disposed through handle 12, receiving member 16 or 16a (not shown in FIG. 7) and insertion member 14 or 14a (not shown in FIG. 7) so as to operatively connect tool head 10 with a drive member 41. (shown schematically in FIG. 7) In FIG. 7, drive rod 46 is shown disposed in partially broken away handle 12 and with insertion member 14 and receiving member 16 removed so as to illustrate the features of drive rod 46. According to the invention, drive rod 46 is separable in similar manner to insertion member 14 and receiving member 16 so that coupling and uncoupling of insertion member 14 and receiving member 16 also provides coupling and uncoupling of drive rod 46. In order to properly separate when insertion member 14 and receiving member 16 are uncoupled, drive rod 46 is preferably provided in two portions 42, 44, and has a coupling structure including head member 48 and grasping member 50 disposed therebetween. Portion 42 is disposed through handle 12 to drive member 41 which may suitably be any conventional grasping or actuating structure such as a scissor handles, while portion 44 is connected to tool head 10 in such a way that longitudinal displacement of rod 46 in the direction of arrow G is translated into the desired motion at tool head 10. As shown in FIG. 7, head member 48 may be disposed on portion 44 and grasping member 50 may be disposed on the other portion 42 of rod 46. Grasping member 50 receives head member 48 when insertion member 14 is inserted into receiving member 16 as shown, for example, by arrow B in FIG. 3. Grasping member 50 and head member 48 engage when insertion member 14 is engage (rotated) with receiving member 16 as by arrow C in FIG. 4. In this manner, convenient and reliable coupling and uncoupling of drive rod 46 is achieved, preferably simultaneous with coupling/uncoupling of insertion member 14 and receiving member 16.

It should be noted that a single groove 22, ridge 20 and arm 28 could be utilized, or that any number of these elements could be provided, as convenient and desired, in any of the embodiments described above. Further, numerous grooves 22 (i.e., groove segments around portions of the inner circumference of receiving member 16) and ridges 20 could be locked/unlocked with a single arm 28 or, preferably, with an arm 28 for each track 24.

It should be noted that while ridge 20 and groove 22 have been shown in the drawings as generally square, they could, of course, be rounded or tapered or of any other shape which may be convenient and desired.

FIG. 8 illustrates an alternate embodiment of the invention, wherein ridges 20b are formed on the inner surface of receiving member 16b, and grooves 22b are formed on protruding portion 18b. Operation of this apparatus would, of course, be similar to that of the embodiment of FIGS. 2-5. In this embodiment, protruding portion 18b could preferably have flatted portions 32 which interact with arms 28b when locking member 26b is extended so as to lock the apparatus against rotation out of the engaged position.

It should also be noted that insertion member 14 and receiving member 16 may preferably be similar to each other and to tool head 10 and handle 12 in outer diameter so as to provide a smooth outer surface. Such a smooth outer surface is, of course, desirable when such an instrument must be inserted into the body of a patient through a cannula.

Thus provided is a coupling apparatus which provides the numerous benefits, as set forth above, of allowing convenient and rapid separation and firm and secure coupling of a tool head and a tool handle.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A coupling apparatus, comprising:
   an insertion member having a protruding portion;
   a receiving member having an inner surface sized to receive the protruding portion of the insertion member wherein the insertion member and the receiving member are substantially tubular in shape and define a continuous inner passage through the coupling apparatus and wherein the receiving member has at least one longitudinal track formed on the inner surface;
   engaging means disposed on the insertion member and the receiving member for coupling the insertion member with the receiving member, the engaging means being rotatable between an engaged position wherein the insertion member and the receiving member are engaged against longitudinal separation, and a disengaged position wherein the receiving member and the insertion member can be longitudinally separated; and
   locking means for locking the engaging means in the engaged position, wherein the locking means comprises at least one longitudinally extending arm member slidably mounted in the at least one longitudinal track and slidable between an extended position wherein the at least one arm member locks the engaging means in the engaged position, and a withdrawn position wherein the engaging means is free to rotate between the engaged position and the disengaged position.

2. An apparatus according to claim 1, wherein the engaging means includes ridge means and groove means for coupling the insertion member with the receiving member, one of the ridge means and groove means being disposed on the insertion member and one of the ridge means and groove means being disposed on the receiving member, the ridge means having a ridge portion and the groove means having a groove portion, rotatable relative to one another between a locked position wherein the ridge portion and the groove portion are locked against longitudinal separation, and an unlocked position wherein the groove portion can be longitudinally separated from the ridge portion.

3. An apparatus according to claim 2, wherein the ridge portion comprises at least one ridge disposed around a portion of an outer circumference of the protruding portion of the insertion member.

4. An apparatus according to claim 3, wherein the groove portion comprises a groove formed around a portion of an inside perimeter of the receiving member.

5. An apparatus according to claim 4, wherein the at least one longitudinal track is sized to accommodate the at least one ridge, and intersects the groove, whereby alignment of the at least one ridge with the at least one longitudinal track allows longitudinal insertion of the insertion member into the receiving member, and whereby rotation of the insertion member relative to the receiving member causes the at least one ridge to engage with the groove.

6. An apparatus according to claim 5, wherein the at least one arm member in the extended position extends into a plane of rotation of the ridge and groove means so as to lock the ridge and groove means in the engaged position.

7. An apparatus according to claim 6, wherein the at least one ridge has two ends, and wherein the at least one arm member abuts both ends of the at least one ridge when the at least one arm member is in the extended position so as to prevent rotation of the insertion member relative to the receiving member when the ridge and groove means are in the engaged position.

8. An apparatus according to claim 6, further including means for biasing the at least one arm member toward the extended position.

9. An apparatus according to claim 8, wherein the at least one arm member has an extending portion disposed inside the receiving member and interacting with the ridge and groove means, and a gripping portion accessible for manipulation through cutouts in the receiving member, whereby the at least one arm member can be manually biased against the biasing means into the withdrawn position so as to facilitate separation of the ridge and groove means.

10. An apparatus according to claim 8, wherein the biasing means is a spring disposed against the locking means so as to bias the at least one arm member toward the extended position.

11. An apparatus according to claim 1, wherein the insertion member and the receiving member are both outwardly substantially round in shape and have substantially the same diameter.

12. An apparatus according to claim 1, wherein the engaging means includes at least one inwardly projecting section and at least one outwardly projecting section, one of the inwardly and outwardly projecting sections being disposed on the insertion member and one of the inwardly and outwardly projecting sections being disposed on the receiving member, rotatable relative to one another between an engaged position wherein the inwardly and outwardly projecting sections are engaged against longitudinal separation and a disengaged position wherein the inwardly and outwardly projecting sections can be longitudinally separated.

13. An apparatus according to claim 1, further including a tool head of a medical instrument attached to the insertion member, and a handle of a medical instrument attached to the receiving member.

14. An apparatus according to claim 13, further including a drive member disposed in the continuous inner passage for actuating the tool head, the drive member having a first portion connected to a drive means and a second portion connected to the tool head.

15. An apparatus according to claim 14, further including means for rotatably engaging the first portion of the drive member with the second portion of the drive member whereby insertion and rotation of the insertion member relative to the receiving member engages the first portion and the second portion of the drive member.

16. A coupling apparatus, comprising:
    an insertion member having a protruding portion;
    a receiving member sized to receive the protruding portion of the insertion member;

engaging means disposed on the insertion member and the receiving member for coupling the insertion member with the receiving member, the engaging means being rotatable between an engaged position wherein the insertion member and the receiving member are engaged against longitudinal separation, and a disengaged position wherein the receiving member and the insertion member can be longitudinally separated; and locking means for locking the engaging means in the engaged position, wherein the locking means is slidably disposed on the insertion member, and wherein the locking means comprises a substantially tubular element slidably and non-rotatably mounted around the protruding portion of the insertion member and having at least one arm member, and wherein the receiving member has at least one longitudinal track sized to receive the at least one arm member when the engaging means is in the engaged position, whereby the locking means locks the engaging means against rotation out of the engaged position.

17. A coupling apparatus, comprising:

an insertion member having a protruding portion;

a receiving member sized to receive the protruding portion of the insertion member;

engaging means disposed on the insertion member and the receiving member for coupling the insertion member with the receiving member, the engaging means being rotatable between an engaged position wherein the insertion member and the receiving member are engaged against longitudinal separation, and a disengaged position wherein the receiving member and the insertion member can be longitudinally separated; and locking means for locking the engaging means in the engaged position, wherein the locking means comprises an arm member slidably and non-rotatably mounted on the insertion member, and wherein the receiving member has at least one longitudinal track sized to receive the arm member when the engaging means is in the engaged position, whereby the locking means locks the engaging means against rotation out of the engaged position.

* * * * *